(12) United States Patent
Walter

(10) Patent No.: US 6,384,040 B1
(45) Date of Patent: May 7, 2002

(54) CONDENSED 4-THIOXOPYRIMIDINE DERIVATIVES AS MICROBICIDES

(75) Inventor: Harald Walter, Rodersdorf (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/601,662

(22) PCT Filed: Feb. 2, 1999

(86) PCT No.: PCT/EP99/00686

§ 371 Date: Aug. 3, 2000

§ 102(e) Date: Aug. 3, 2000

(87) PCT Pub. No.: WO99/40074

PCT Pub. Date: Aug. 12, 1999

(30) Foreign Application Priority Data

Feb. 4, 1998 (GB) .............................. 9802355

(51) Int. Cl.⁷ ...................... C07D 495/04; A01N 45/54
(52) U.S. Cl. ........................ 514/258; 544/278
(58) Field of Search ............................. 544/278; 514/258

(56) References Cited

FOREIGN PATENT DOCUMENTS

| WO | WO94/26722 | 11/1994 |
|---|---|---|
| WO | WO97/02262 | 1/1997 |
| WO | WO97/33890 | 9/1997 |

OTHER PUBLICATIONS

Abstracts of Japan, vol. 009, No. 036, Feb. 15, 1985, Abstract of Patent Publication 59–181265, published Oct. 15, 1984.

"Deamination Studies on Pyrimidine and Condensed by Pyrimidine Systems", vol. 29,, pp. 2674–2677, XP002107725, 1964, R. B. Trattner et al.

*Primary Examiner*—John M. Ford
(74) *Attorney, Agent, or Firm*—William A. Teoli, Jr.

(57) ABSTRACT

Novel 4-thioxopyrimidine compound of formula I

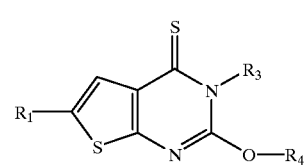

(I)

wherein $R_1$ is chlorine or bromine and $R_3$ and $R_4$ are independently propyl or butyl, in the free form or in salt form; exhibit useful biological properties for controlling phytopathogenic microbicides.

The novel compounds may be used in the agricultural field for controlling of mircobicides on crop plants, e.g. phytopathogenic fungi.

6 Claims, No Drawings

CONDENSED 4-THIOXOPYRIMIDINE DERIVATIVES AS MICROBICIDES

This application is a US National Phase Application filed under 35 USC 371 of PCT/EP99/00686 filed Feb. 2, 1999.

The present invention relates to compounds of formula I, which have microbicidal activity, in particular fungicidal activity. The invention also relates to the preparation of these substances, to agrochemical compositions which comprise at least one of the novel compounds as active ingredient, to the preparation of the compositions mentioned and to the use of the active ingredients or compositions inite a Mric eulture for controlling or preventing infestation of plants by phytopathogenic microorganisms, preferably fungi.

The 4-thioxopyrimidines according to the invention have the general formula I

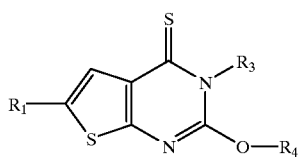

(I)

wherein $R_1$ is chlorine or bromine and $R_3$ and $R_4$ are independently propyl or butyl.

4-Pyrimidinones with fungicidal properties useful in agricultural practice are known from U.S. Pat. No. 3,755,582, WO 94/26722, WO 97/02262 and WO 97/33890. The disclosed compounds for practical purposes do not always satisfy the needs of the modern agriculture.

Surprisingly, it has now been found that the thieno[2,3-d]pyrimidine derivatives of formula I exhibit improved biological properties which render them more suitable for the practical use in agriculture and horticulture.

The compounds of formula I may be obtained in the form of their acid addition salts. Such acid addition salts are, for example, formed with mineral acids, typically sulfuric acid, a phosphoric acid or a hydrogen halide, with organic carboxylic acids, typically acetic acid, oxalic acid, malonic acid, maleic acid, fumaric acid or phthalic acid, with hydroxycarboxylic acids, typically ascorbic acid, lactic acid, malic acid, tartaric acid or citric acid, or with benzoic acid, or with organic sulfonic acids, typically methanesulfonic acid or p-toluenesulfonic acid.

Within the present specification propyl and butyl denote n-propyl, isopropyl, n-butyl, sec-butyl, isobutyl and tert-butyl. Non-branched alkyl is preferred.

Preferred individual compounds are:
- 6-chloro-2-propoxy-3-propyl-4-thioxo-thieno[2,3-d]pyrimidine,
- 3-butyl-6-chloro-2-propoxy-4-thioxo-thieno[2,3-d]pyrimidine,
- 6-bromo-2-propoxy-3-propyl-4-thioxo-thieno[2,3-d]pyrimidine, and
- 6-bromo-3-butyl-2-propoxy-4-thioxo-thieno[2,3-d]pyrimidine.

The compounds of formula I may be obtained by treatment of a compound of formula II

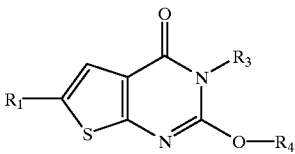

(II)

wherein $R_1$, $R_3$ and $R_4$ are as defined for formula I, with a sulfurating agent, e.g. $P_2S_5$ or the Lawesson reagent. The reaction conditions for sulfurating reactions of this type are well known in the art (B. A. Jones, J. S. Bradstaw, Chem. Rev. 1984 (84), 17–30) and for the purpose of present invention is conveniently carried out in analogy to known procedures. Advantageously, the reaction is carried out in an inert solvent, e.g. dioxane, tetrahydrofurane, toluene, xylene and the like, and at a temperature in the range of the boiling point of the reaction mixture, conveniently at reflux. The starting material of formula II is known from the prior documents cited above.

Alternatively, the compounds of formula I may be obtained by alcoholysis of a compound of formula III

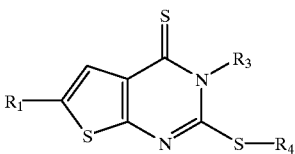

(III)

wherein $R_1$, $R_3$ and $R_4$ are as defined for formula I, in the presence of a base with an alcohol of formula IV $$HO-R_4 \quad (IV)$$

Suitably the base is selected from the alkali salts of the employed alcohol, and the reaction is carried out in an excess of the alcohol which may at the same time serve as solvent. In a variant the alcohol may be employed only in slight excess, and an inert solvent may be employed.

The starting material of formula III has especially been developed for the present invention. It is therefore another part of this invention.

The compounds of formulae I and III may be obtained according to the following schemes:

Scheme 1
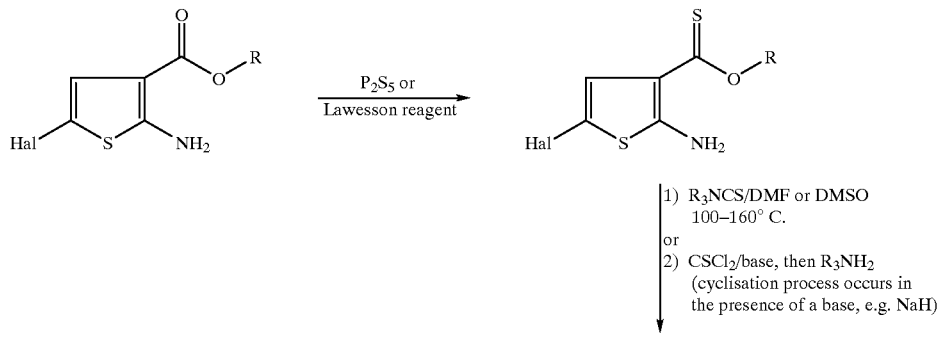
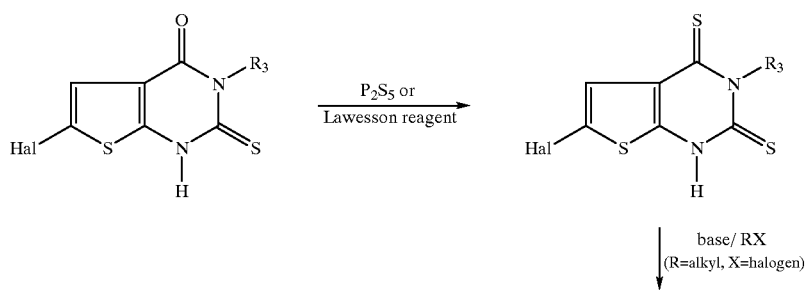
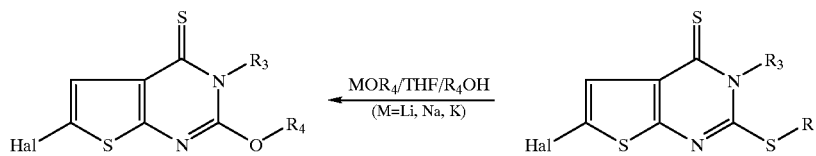
Scheme 2
[NXS = N-Hal-Succinimide]
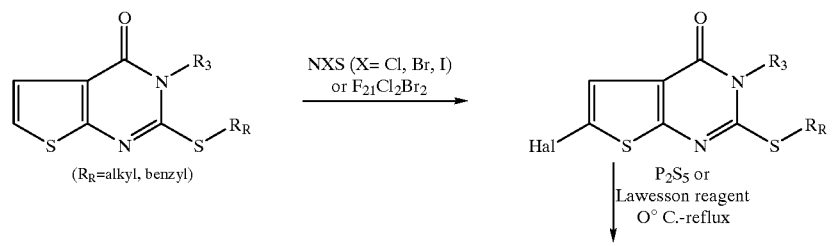
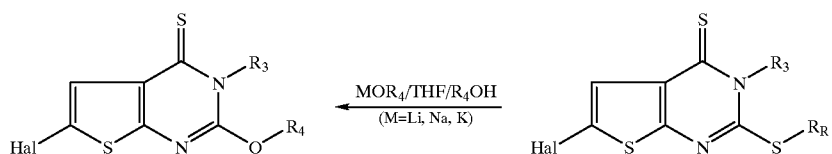

Scheme 3

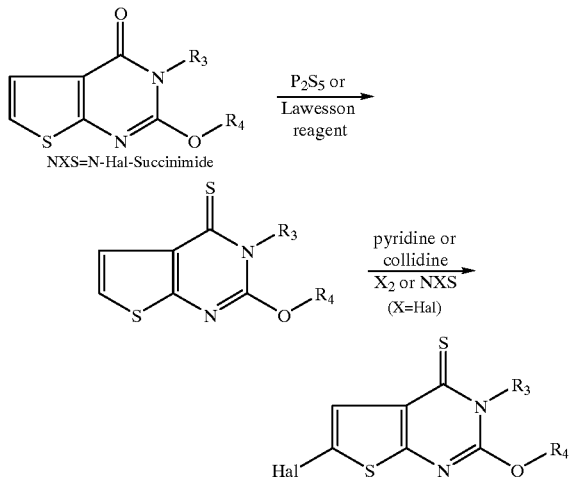

NXS=N-Hal-Succinimide

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. Botrytis, Pyricularia, Helminthosporium, Fusarium, Septoria, Cercospora and Alternaria) and Basidiomycetes (e.g. Rhizoctonia, Hemileia, Puccinia). Additionally, they are also effective against the Ascomycetes classes (e.g. Venturia and Erysiphe, Podosphaera, Monilinia, Uncinula) and of the Oomycetes classes (e.g. Phytophthora, Pythium, Plasmopara). Outstanding activity has been observed against powdery mildew (Erysiphe spp.). Furthermore, the novel compounds of formula I are effective against phytopathogenic bacteria and viruses (e.g. against Xanthomonas spp, Pseudomonas spp, *Erwinia amylovora* as well as against the tobacco mosaic virus).

Within the scope of present invention, target crops to be protected typically comprise the following species of plants: cereal (wheat, barley, rye, oat, rice, maize, sorghum and relate species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflower, coconut, castor oil plants, cocoa beans, groundnuts); cucumber plants (pumpkins, cucumbers, melons); fibre plants (cotton, flax, hemp, jute); citrus fruit (oranges, lemons, grapefruit mandarins); vegetables (spinache, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilisers, antifoams, viscosity regulators, binders or tackifiers as well as fertilisers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilisers. Such carriers are for example described in WO 97/33890.

The compounds of formula I are normally used in the form of compositions and can be applied to the crop area or plant to be treated, simultaneously or in succession with further compounds. These further compounds can be e.g. fertilisers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The 4-thioxopyrimidines of formula I in general exhibit a relative lower vapor pressure than the analogous 4-pyrimidinones. The compounds of formula I surprisingly show improved antifungal activity in leaf treatment application in climate zones with relatively warm average temperatures during the application period. As a further advantage of the compounds of formula I an extended period of protection of the treated plants against fungal attack is observed. Accordingly, the compounds of formula I provide improved biological performance properties for the agricultural practice by requiring less frequent repetition of the application, and at the same time providing equal or improved level of protection.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl, carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129 or 2-[α{[(α-methyl-3-trifluoromethyl-benzyl)imino]-oxy}-o-tolyl]-glyoxylic acid-methylester-O-methyloxime; dithiocarbamates such as ferbam, mancozeb, maneb, metiram, propineb, thiram, zineb or ziram; N-halomethylthiodicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothalisopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine or validamycin.

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregne ting the seeds or tubers either with a liquid formulation of the fungicide or coating them with a solid formulation.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Example illustrates the above-described invention in more detail. Temperatures are given in degrees Celsius. The following abbreviations are used: m.p.=melting point; b.p.=boiling point. "NMR" means nuclear magnetic resonance spectrum. MS stands for mass spectrum. "%" is percent by weight, unless corresponding concentrations are indicated in other units.

PREPARATION EXAMPLE

Example P1: 6-Chloro-2-propoxy-3-propyl-4-thioxo-thieno[2,3-d]pyrimidine

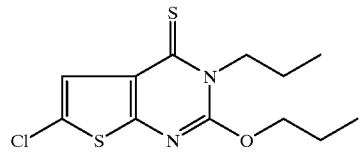

In a sulfonation flask, a mixture of 1.15 g 6-chloro-2-propoxy-3-propyl-4-oxo-thieno[2,3-d]pyrimidine, 0.97g Lawesson reagent and 50 ml of dioxane is heated at reflux temperature for 3.5 hours. After removal of the solvent in the water jet vacuum, the residue is taken up in ethylacetate and the organic phase is washed twice with water. The organic phase is dried over sodium sulfate and the solvent removed in the water jet vacuum. The crude material is purified twice by column chromatography over silica gel (eluant: tert. butylmethylether/hexane 1:9). Yield: 0.3 g pure 6-chloro-2-propoxy-3-propyl-4thioxo-thieno[2,3-d]pyrimidine in the form of a yellow powder; m.p. 81–83° C.

The compounds of the following table may be obtained in analogous manner or by similar methods corresponding to those indicated above.

TABLE

| cmpd. No. | $R_1$ | $R_3$ | $R_4$ | phys. data (m.p. ° C.) |
|---|---|---|---|---|
| 1 | Cl | $C_3H_7$-n | $C_3H_7$-n | 81–83° C. |
| 2 | Br | $C_3H_7$-n | $C_3H_7$-n | 110–112° C. |
| 3 | Cl | $C_4H_9$-n | $C_3H_7$-n | 68–70° C. |
| 4 | Br | $C_4H_9$-n | $C_3H_7$-n | 95–97° C. |
| 5 | Cl | $C_4H_9$-i | $C_3H_7$-n | |
| 6 | Br | $C_4H_9$-i | $C_3H_7$-n | oil |
| 7 | Cl | $C_3H_7$-n | $C_3H_7$-i | |
| 8 | Br | $C_3H_7$-n | $C_3H_7$-i | |
| 9 | Cl | $C_4H_9$-n | $C_3H_7$-i | |
| 10 | Br | $C_4H_9$-n | $C_3H_7$-i | |
| 11 | Cl | $C_4H_9$-i | $C_3H_7$-i | |
| 12 | Cl | $C_3H_7$-n | $C_4H_9$-n | |
| 13 | Br | $C_3H_7$-n | $C_4H_9$-n | |
| 14 | Cl | $C_4H_9$-n | $C_4H_9$-n | 52–54° C. |
| 15 | Br | $C_4H_9$-n | $C_4H_9$-n | |
| 16 | Cl | $C_4H_9$-i | $C_4H_9$-n | |
| 17 | Cl | $C_3H_7$-n | $C_4H_9$-i | |
| 18 | Br | $C_3H_7$-n | $C_4H_9$-i | |
| 19 | Cl | $C_4H_9$-n | $C_4H_9$-i | |
| 20 | Br | $C_4H_9$-n | $C_4H_9$-i | |
| 21 | Cl | $C_4H_9$-i | $C_4H_9$-i | |

Formulation Examples for Compounds of Formula I

Working procedures for preparing formulations of the compounds of formula I such as Emulsifiable concentrates, Solutions, Granulates, Dusts and Wettable powders are described in WO 97/33890.

BIOLOGICAL EXAMPLES: FUNGICIDAL ACTIONS

Example B-1: Action Against *Erysiphe graminis* on Barley a) Residual-protective Action Barley plants about 8 cm in height are sprayed to drip point with a spray mixture (0.02% a.i.) prepared from a wettable powder formulation of the test compound, and the treated plants are dusted with conidia of the fungus 3 to 4 hours later. The infected plants are stood in a greenhouse at 22° C. Evaluation of the fungal infection is made 12 days after infection. Compounds 1 to 4,6 and 14 showed complete control activity in this test. Compounds 1,2,3 and 4 exhibited over 80% control of the fungal infection at a concentration of 0.2 ppm.

b) Systemic Action

Barley plants about 8 cm in height are drenched with an aqueous spray mixture (0.002% a.i., based on the volume of the soil) prepared from a wettable powder formulation of the test compound. Care is taken that the spray mixture does not come into contact with the growing parts of the plants. The treated plants are dusted 48 hours later with conidia of the fungus. The infected plants are then stood in a greenhouse at 22° C. Evaluation of the fungal infestation is made 12 days after infection. Compounds 1 to 4 exhibited over 80% control of the fungal infection in this test.

Example B-2: Action Against *Podosphaera leucotricha* on Apple Shoots

Apple cuttings with fresh shoots about 15 cm long are sprayed with a spray mixture (0.06% a.i.). The plants are infected 24 hours later with a conidia suspension of the fungus and stood in a climatic chamber at 70% relative humidity and 20° C. Evaluation of the fugal infestation is made 12 days after infection. Compounds of the Table show good activity in this test.

Example B-3: Action Against *Uncinula necator* on Vines 5 week old vine cuttings are sprayed with a spray mixture (200 ppm a.i.) prepared from a wettable powder formulation of the test compound. The plants are infected 24 hours later by conidias from strongly infested vine leafs that are shaken off over the test plants. The plants are then incubated at 26° C. and 60% relative humidity. The evaluation of the fungal infestation is made ca. 14 days after infection. Compounds 1,2,3,4,6 and 14 showed complete control activity in this test. Compounds 1, 2,3 and 4 exhibited over 80% control of the funga infection at a concentration of 0.2 ppm.

What is claimed is:

1. A 4-thioxopyrimidine compound of formula I

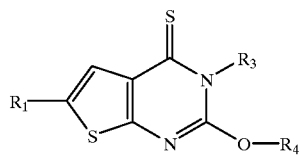

(I)

wherein $R_1$ is chlorine or bromine and $R_3$ and $R_4$ are independently propyl or butyl.

2. A process for the preparation of compounds of formula I as defined in claim 1 which comprises treatment of a compound of formula II

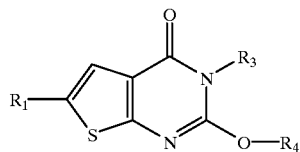

(II)

wherein $R_1$, $R_3$ and $R_4$ are as defined for formula I, with a sulfurating agent.

3. The process of claim 2 wherein said sulfurating agent is $P_2S_5$ or the Lawesson reagent.

4. A composition for controlling microognisms and preventing attack and infestation of plants therewith, wherein the active ingredient is a compound as claimed in claim 1 together with a suitable carrier.

5. A method of controlling or preventing infestation of cultivated plants by phytopathogenic microorganisms by application of an effective amount of a compound of formula I as claimed in claim 1 to plants, to parts thereof or to the locus thereof.

6. A compound of formula III

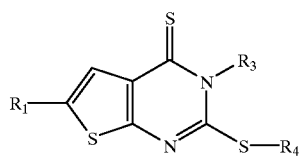

(III)

wherein $R_1$, $R_3$ and $R_4$ are as defined in claim 1.

* * * * *